United States Patent

Baker et al.

Patent Number: 5,093,111
Date of Patent: Mar. 3, 1992

[54] LIPSTICK COMPOSITION COMPRISING CETEARYL ISONONANOATE, A SESQUISTEARATE AND ISOPROPYL HYDROXYSTEARATE

[75] Inventors: Christopher G. Baker, Port Jervis, N.Y.; Richard D. Berg, Milford, Pa.

[73] Assignee: Kolmar Laboratories Inc., Port Jervis, N.Y.

[21] Appl. No.: 667,802

[22] Filed: Mar. 11, 1991

[51] Int. Cl.$^5$ .............................. A61K 7/025
[52] U.S. Cl. .................. 424/64; 424/DIG. 5; 424/63; 514/873
[58] Field of Search .............. 424/78, 60, 81, 64, 424/63, DIG. 5; 514/873

[56] References Cited

U.S. PATENT DOCUMENTS

| | | | |
|---|---|---|---|
| 4,795,631 | 1/1989 | Sheehan | 424/81 |
| 4,820,508 | 4/1989 | Wortzman | 424/60 |
| 4,883,659 | 11/1989 | Goodman et al. | 424/78 |

Primary Examiner—Thurman K. Page
Assistant Examiner—D. Colucci
Attorney, Agent, or Firm—Andrus, Sceales, Starke & Sawall

[57] ABSTRACT

A lipstick composition comprising by weight from 8% to 20% of waxes, 30% to 80% of oils, 3% to 30% of colorants, 8% to 20% of cetearyl isononanoate, 1% to 10% of a sesquistearate and 2% to 20% of isopropyl hydroxystearate. The lipstick has the aesthetic performance characteristics of a regular lipstick but more effectively soothes and protects the lips.

4 Claims, No Drawings

LIPSTICK COMPOSITION COMPRISING CETEARYL ISONONANOATE, A SESQUISTEARATE AND ISOPROPYL HYDROXYSTEARATE

BACKGROUND OF THE INVENTION

Traditionally, lipsticks have been formulated as a combination of waxes, oils and colorants, wherein the wax forms a supporting framework or matrix in which the oils and colorants are suspended. Lipstick compositions have also been modified by the incorporation of semi-solid materials, such as lanolin, lanolin derivatives and various long chain esters which provide a more uniform application, a pleasant or creamy feel on the lips and a shiney appearance.

However, there have been certain disadvantages to these modified lipsticks which center around the movement of the product after it is applied to the lips. As a result, plasticizers have been added to the lipstick composition which allow the lipstick to accommodate higher levels of wax without compromising the improved uniform application and creamy feel provided by the semisolid materials.

Recently, there has been considerable activity in the production of cosmetic products in the form of creams and lotions designed to protect and moisturize the skin. However, these products in general have not been offered to protect the lips and the type of product available on the market for lip protection has taken the form of heavy creams, ointments and solid colorless sticks designed primarily to seal the lips with an occlusive barrier. Therefore, there has been a need for a lipstick that protects and moisturizes the lips while retaining the aesthetic benefits of a conventional lipstick.

SUMMARY OF THE INVENTION

The invention relates to a lipstick composition having the aesthetic performance of a conventional lipstick but providing added benefits of lip protection. In general, the lipstick composition comprises by weight from 8% to 20% of waxes, 30% to 80% of oils, 3% to 30% of colorants, 8% to 20% of cetearyl isononanoate, 1% to 10% of a sesquistearate, such as methyl glucose sesquistearate or sorbitan sesquistearate, and 2% to 20% of isopropyl hydroxystearate.

The cetearyl isononanoate acts as a plasticizer or wax softener, providing a smooth application and enabling the composition to remain pliable on the lips.

The sesquistearate further aids in improving the application qualities of the lipstick, plasticizing the wax to enhance its spreadability, while the isopropyl hydroxystearate acts as a pigment wetting agent and an emollient.

The lipstick composition of the invention, including the cetearyl isononanoate, the sesquistearate and the isopropyl hydroxystearate provides a composition that protects and moisturizes the lips while retaining the aesthetic benefits of a regular or conventional type of lipstick.

DESCRIPTION OF THE PREFERRED EMBODIMENT

The lipstick composition of the invention has the following composition in weight percent:
Waxes: 8%-20%
Oils: 30%-80%
Colorants: 3%-30%
Cetearyl Isononanoate: 8%-20%
Sesquistearate: 1%-10%
Isopropyl hydroxystearate: 2%-20%

The preferred formulation of the lipstick in weight percent is as follows:
Waxes: 12%-16%
Oils: 50%-70%
Colorants: 8%-16%
Cetearyl Isononanoate: 8%-14%
Sesquistearate: 1%-5%
Isopropyl hydroxystearate: 5%-15%

The wax to be used in the lipstick composition can either be natural or synthetic waxes of the type conventionally used in cosmetic formulations. More particularly, the wax can take the form of candelilla, carnauba, ozokerite, ceresin, white beeswax, yellow beeswax, paraffin and petroleum-derived waxes.

Either natural or synthetic oils of the type commonly used in cosmetic products can be employed. Specific examples of oils that can be used include mineral oil, olive oil, castor oil, lanolin oil, sesame oil, persic oil, soybean oil, squalene, and fatty acids such as isopropyl myristate, isopropyl palmitate and the like.

Specific examples of colorants that can be incorporated into the lipstick are as follows: D&C Red No. 6 Barium Lake, D&C Red No. 7 Calcium Lake, D&C Red No. 27 Aluminum Lake, D&C Red No. 33 Aluminum Lake, FD&C Yellow No. 5 Aluminum Lake, titanium dioxide, iron oxides, mica, bismuth oxychloride and the like.

In the composition, the wax forms a supporting matrix in which the oils and colorants are suspended.

The cetearyl isononanoate acts as a plasticizer or wax softener, preventing the lipstick from forming a hard structure, thus retaining the composition in a pliable state on the lips and giving a smooth application. In addition, the material acts as an emollient and a solvent for the dyes.

The sesquistearate can be selected from methyl glucose sesquistearate or sorbitan sesquistearate and mixtures thereof, and provides "fine tuning" of the lipstick's application characteristics and further plasticizing of the waxes, thus enhancing its spreadability.

The isopropyl hydroxystearate serves as a pigment wetting agent and emollient, thus enhancing color development and also protecting the lips.

In addition to the above ingredients, the lipstick composition can contain up to 3% by weight of fragrances, and up to 1% by weight of preservatives such as BHA, vitamin E, ascorbyl palmitate, or the like.

Specific examples of the lipstick composition of the invention are as follows:

EXAMPLE 1

Castor Oil: 49.50%
Cetearyl Isononanoate: 10.00%
Isopropyl hydroxystearate: 10.00%
Mineral Oil: 4.00%
Candelilla Wax: 6.00%
Ozokerite: 4.00%
Paraffin: 4.00%
Carnauba Wax: 1.00%
Methyl Glucose Sesquistearate: 1.00%
Colorants: 10.00%
Fragrance/Flavor: 0.35%
Preservatives: 0.15%

EXAMPLE 2

Castor Oil: 39.50%
Cetearyl Isononanoate: 12.00%
Isopropyl hydroxystearate: 15.00%
Olive Oil: 4.00%
Lanolin: 3.00%
Candelilla Wax: 5.00%
Beeswax: 3.00%
Ozokerite: 3.00%
Paraffin: 2.00%
Carnauba Wax: 2.00%
Methyl Glucose Sesquistearate: 1.00%
Colorants: 10.00%
Fragrance/Flavor: 0.35%
Preservatives: 0.15%

EXAMPLE 3

Castor Oil: 46.50%
Cetearyl Isononanoate: 12.00%
Isopropyl hydroxystearate: 8.00%
Mineral Oil: 3.00%
Lanolin Oil: 3.00%
Candelilla Wax: 5.00%
Beeswax: 3.00%
Ceresin: 5.00%
Carnauba Wax: 2.00%
Sorbitan Sesquistearate: 2.00%
Colorants: 10.00%
Fragrance/Flavor: 0.35%
Preservatives: 0.15%

The lipstick composition of the invention not only has aesthetic performance characteristics typical of a conventional lipstick, but provides increased protection and moisturization for the lips.

Various modes of carrying out the invention are contemplated as being within the scope of the following claims particularly pointing out and distinctly claiming the subject matter which is regarded as the invention.

We claim:

1. A lipstick composition, comprising by weight from 8% to 20% of a cosmetically acceptable wax, 30% to 80% of a cosmetically acceptable oil, 3% to 30% of colorants, 8% to 20% of cetearyl isononanoate, 1% to 10% of a material selected from the group consisting of methyl glucose sesquistearate and sorbitan sesquistearate and mixtures thereof, and 2% to 20% isopropyl hydroxystearate.

2. The lipstick composition of claim 1, wherein said wax is selected from the group consisting of candelilla, carnauba, ozokerite, ceresin, white beeswax, yellow beeswax paraffin and petroleum-derived waxes.

3. The lipstick composition of claim 1, wherein said oil is selected from the group consisting of mineral oil, olive oil, castor oil, lanolin oil, sesame oil, persic oil, soybean oil, squalene, and fatty esters.

4. A lipstick composition having improved protection and moisturization for the lips, comprising 12% to 16% of a cosmetically acceptable wax, 50% to 70% of a cosmetically acceptable oil, 8% to 16% colorants, 8% to 14% of cetearyl isononanoate, 1% to 5% of sesquistearates selected from the group consisting of methyl glucose sesquistearate and sorbitan sesquistearate and mixtures thereof, and 5% to 15% of isopropyl hydroxystearate.

* * * * *